United States Patent [19]

Bisping

[11] 4,106,512

[45] Aug. 15, 1978

[54] TRANSVENOUSLY IMPLANTABLE LEAD

[75] Inventor: Hans Jurgen Bisping, Aachen, Fed. Rep. of Germany

[73] Assignee: Medtronic, Inc., Minneapolis, Minn.

[21] Appl. No.: 751,226

[22] Filed: Dec. 16, 1976

[51] Int. Cl.² .............................................. A61N 1/04
[52] U.S. Cl. ................................. 128/418; 128/419 P
[58] Field of Search ............... 128/2.06 E, 2.1 E, 404, 128/418, 419 P, DIG. 4

[56] References Cited

U.S. PATENT DOCUMENTS

| 3,416,534 | 12/1968 | Quinn | 128/419 P |
|---|---|---|---|
| 3,827,428 | 8/1974 | Hon et al. | 128/418 X |
| 3,902,501 | 9/1975 | Citron et al. | 128/418 |
| 3,943,936 | 3/1976 | Rasor et al. | 128/419 P |
| 3,974,834 | 8/1976 | Kane | 128/418 |
| 4,000,745 | 1/1977 | Goldberg | 128/418 |
| 4,026,303 | 5/1977 | Babotai | 128/418 |

Primary Examiner—William E. Kamm
Attorney, Agent, or Firm—Lew Schwartz; Joseph F. Breimayer; Harry W. Barron

[57] ABSTRACT

A body-implantable, intravascular lead affixed with a pin or pins at its proximal end adapted to be connected to a cardiac pacemaker pulse generator and with an electrode or electrodes at its distal end adapted to be securely and permanently attached to a body organ through endothelial tissue. An electrode in spiral shaped form of a rigid, electrically conductive helix with a sharp tip at the distal end of the lead is adapted to be screwed through endothelial tissue into the body organ by means of a rotational motion applied to the conductor at the proximal end of the lead.

21 Claims, 4 Drawing Figures

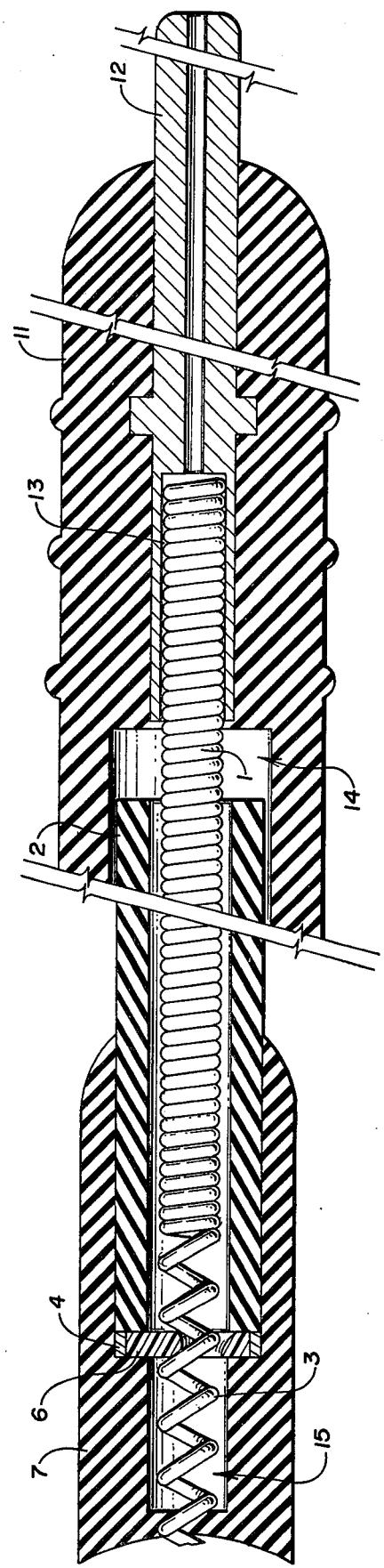

TRANSVENOUSLY IMPLANTABLE LEAD

BACKGROUND OF THE INVENTION

This invention relates to a lead bearing an electrode for connecting a living organ to an electrical device. Notwithstanding its various uses, this invention will be described as a transvenously implantable pacing and sensing lead for connecting a pacemaker to cardiac tissue.

Pacemaker leads represent the electrical link between the pulse generator and the heart tissue which is to be excited. Two methods are known for the long-lasting implantation of such leads (W. Hager, A. Seling, Praxis der Schrittmachertherapie; F. K. Schattauer Verlag 1974 — Practice of pacemaker therapy; F. K. Schattauer publishers, 1974):

1. Following thoracotomy and pericardiotomy the electrode at the distal end of the lead is sewed onto the myocardium tissue, or else screwed from outside into this tissue with the help of a special device. This technique requires relatively important surgery, with the corresponding risks, so that it is not always applied, particularly in the case of elderly patients.

2. With the transvenous implantation method, which can also be made under local anesthesia, the electrode is pushed into the heart through a vein. Difficulties arise with this method from the tendency to a dislodging of non-fixable electrode heads as a result of heart motions and blood flow. More particularly, when the electrode is to be fixed in the atrium, this being often desirable from the medical point of view, the risk of dislodging is high, because of the smoothness of the atrial wall muscle.

Because of this, it has been proposed to use other types of electrodes which are designed so as to be firmly anchored in the heart by means of mechanical fixation devices in the form of metal or plastic hooks.

With one of these systems, the lead carries on its distal end a wire counter-hook requiring that the lead be pushed through a voluminous guide tube. The selection of the stimulating location in the heart is rendered much more difficult by the stiffness of the guide tube. Similarly, retracting the lead is possible only with the help of the guide tube, because the wire hook is protruding.

With other hook systems, use is made of the pressure of a guiding wire (stylet) placed inside the electrode, to drive and to push into the heart tissue a hook device which must be retracted during the introduction phase. Various embodiments of this system employ either nylon brushes or small steel hooks, but these have no real "counter-hook" effect. A secure firm hooking is achievable with all these systems only when the electrode head lies perpendicular to the tissue. If electrodes of this type come to rest at an acute angle, it can happen that only one of the hooks will grip, and that the electrode will be dislodged by forces oriented in a corresponding direction, such as may result from blood flow or heart motions.

When such electrodes have to be withdrawn from the heart, the hook device must be pulled back with a nylon thread, according to one system, or else, with another type of electrode, the electrodes are pulled back together with the released hooks.

It is therefore an objective for the electrode according to the present invention to be easily implanted through a vein and without requiring an auxiliary device. It should above all, to meet the requirements of an optimal electrotherapy of the heart, provide for a reliable fixation in the smooth wall of the atrium. If the need should arise, during the implantation, to place the electrode in a location other than the one found at first, the electrode according to the invention should then be released easily after its fixation, so as to be shifted to another location.

SUMMARY OF THE INVENTION

The above features and advantages of the present invention, as well as others, are accomplished by providing a body-implantable, intravascular lead comprising electrical conductors connected at the proximal end of the lead to a suitable connector itself adapted to be connected to a source of electrical energy, and electrode means at the distal end of the lead affixed to the conductor and adapted to be firmly lodged in and permanently secured to or removeable from tissue inside the body at a desired location. The conductor and the portion of the electrode means affixed to the conductor are sealed from living animal body fluids and tissue by a material substantially inert to body fluids and tissue. Sheath means are provided for permitting the lead means and electrode means to be inserted into and guided through a body vessel to a desired location and position inside the body without causing injury to the body vessel and for permitting the electrode means to be firmly lodged in and permanently secured to body tissue at the desired location. Preferably, the electrode means comprises a helix or corkscrew of a suitable electrode material within the sheath means.

More particularly, the object and advantages of the invention are realized in a preferred embodiment by the additional provision of means for applying rotational torque to the length of conductor outside the heart for rotating the electrode means to screw it from the sheath means into (or from on removal) heart muscle.

According to the invention, the terminal portion, adapted to be located inside the heart, of the flexible and otherwise closely wound, coiled conductor is loosely wound with a long pitch, and the resulting helix having a corkscrew shape is screwed into the heart muscle by applying a torque to the other end of the said conductor without requiring the use of any further auxiliary device. In this manner, operating like a flexible transmission shaft, the inner conductor is twisted against the outer sheath. According to a preferred embodiment of the invention, the electrical conductor is constituted by the closely wound conductor which is placed inside an insulating flexible tube.

According to a further embodiment of the invention, an element located in the electrode head operates for driving the helix out of the protective sheath means, or to retract it inside it, according to the sense of rotation. Through a mechanical limitation of the rotation angle and/or through markings identifiable by X-rays, which show clearly the positions of the protective sheath and of the helix, respectively to each other, it is ensured that the helix is screwed into the tissue only to the provided extent (about 2 - 4 mm).

The structure according to the invention has a number of important advantages. The helical shape of the electrode provides for a reliable fixation in the heart tissue since its removal is only possible by unscrewing it. A repeated fixation attempt can be made immediately after unscrewing, without having to pull back the electrode from inside the heart. After fixation, forces from practically any direction can apply to the electrode head, without the electrode becoming dislodged.

The insertion of the lead, the diameter of which is not different from that of non-fixable transvenous leads, requires no guide tube. The fixation operation does not require a guide wire (stylet) which would impair the flexibility of the device; the angle at which the electrode should come to rest against the tissue is to a large extent without any influence and there is no need to take care of securing an anchoring of small hooks on all sides.

Other features, advantages and objects of the present invention will hereinafter become more fully apparent from the following description of the drawings, which illustrate preferred embodiments thereof.

BRIEF DESCRIPTION OF THE DRAWINGS

FIG. 4 shows a still further embodiment in longitudinal sectional compressed in length, of an electrode head and the remaining elements of the lead design common to all embodiments shown in the drawings.

DESCRIPTION OF THE PREFERRED EMBODIMENT

Referring now to the preferred embodiments of the invention depicted in the figures it should be noted that the intravascular transvenous lead comprises in each instance an elongated conductor 1, a distal electrode bearing end and a proximal end (shown only in FIG. 4). In all four figures, the helix 3 is shown in its retracted position.

Figure 1:
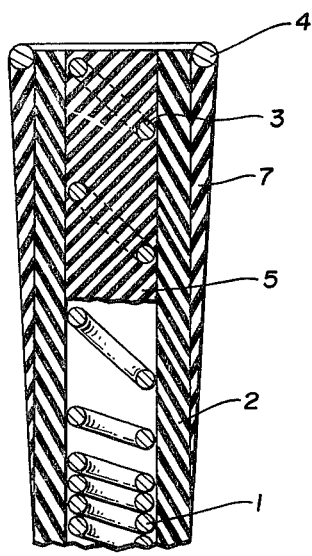
FIG. 1 shows a view in part of a preferred embodiment of the body-implantable, transvenous lead of the present invention depicting an inside elevation in longitudinal cross-section of the electrode head.

FIG. 1 represents an axial cross-section of the distal end or electrode head of the lead, with the helix 3 lying inside a protection sheath or tube 2. Preferably, an electrode head of this type is designed in such manner that the inner electrical conductor 1 is formed of helically, closely wound wire, and that at its end 3 inserted in the heart, it is coiled loosely for about 10 mm length, that is with a longer winding pitch. The external sheath of the electrode consists preferably of a flexible tube 2 made of insulating material, e.g. silicone rubber, inside which the inner conductor 1 can be easily rotated. In this embodiment, the insulating tube 2 serves simultaneously as an electrode head at the distal end of the lead and as a protective sheath for the loosely wound helix 3 comprising the electrode, which must not cause any lesions during the introduction phase through the veins and heart valves. Preferably, the forward end of the helix 3 is ground so as to form a sharp point. The insulating tube comprises also, at the electrode head, the element 5 which causes the helix to be driven axially when the internal conductor is rotated. This effect can be achieved for instance, as shown in FIG. 1, by forming the element 5 as a cylinder of silicone rubber provided with a helical passage or grooves in which the loosely coiled helix 3 can easily rotate.

Figure 2:
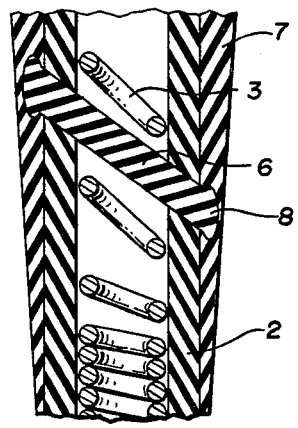
FIG. 2 shows a further embodiment of the electrode head in longitudinal cross-section.

FIG. 2 shows another embodiment of the electrode head, seen in longitudinal cross-section. The conversion of the rotary motion into an axial motion is obtained here by means of one or more plastic (e.g. Teflon) wires 6 which is helically wound with the same pitch as the helix 3. The plastic wire 6 is inserted inside the insulating tube 2 to which its ends are welded, forming small butts 8 which hold it in place and prevent its sliding out.

A ring 4, preferably metallic and coated with an insulating material, is attached to the end of tube 2 by means of a silicone rubber sheath cover 7. This ring serves, in both embodiments of FIG. 1 and FIG. 2, to ascertain by X-ray examination, how far the helix 3 on the inner conductor 1 has been screwed beyond the protection sheath 2. The outer cover 7 serves further, in the embodiment of FIG. 2, to mask the butts 8 so as to prevent the formation of a thrombosis. In the embodiments of FIGS. 1 and 2 the elements 5 and 6 constitute stop-pieces when the helix 3 is fully advanced, since the more closely spaced turns of conductor 1 cannot be passed through these elements unless a stronger torque is applied in turning conductor 1.

Figure 3:
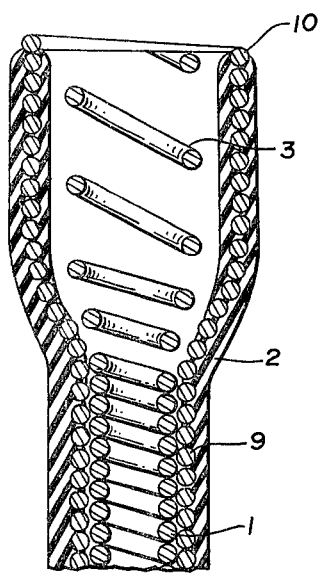
FIG. 3 shows a still further embodiment of the electrode head in longitudinal cross-section.

FIG. 3 shows a further preferred embodiment of the electrode head, also in longitudinal cross-section. Here is again shown the inner coiled wire conductor 1 which simultaneously provides the electrical connection from the pulse generator to the electrode. The forward end of this conductor is again wound with a long pitch, so as to allow it to be screwed into the tissue. As an additional feature, the diameter of the helix 3 can be increased, as well as that of an external helical conductor 9 at the distal end of the electrode. The axial motion is achieved by turning the inner conductor 1 in sliding contact over a certain length with the inner surface formed by the turns of an external co-axial conductor 9 which is similarly closely wound into a helix having a larger diameter than conductor 1, so that a screwing effect is made possible. At the distal end of the lead, the external conductor 9 terminates into a ring electrode 10 which is not insulated by the silicon cover 2, so that the tissue may already be stimulated through this ring electrode 10 before the helix 3 is screwed into the tissue. The closely wound, external, co-axial conductor 9 achieves a rigid metal cylinder, externally insulated, the inner wall of which creates threaded spiral grooves for receiving the turns of the conductor 1.

Turning now to FIG. 4, there is shown a further embodiment of the lead of the present invention combining several of the features of the preceding figures together with means 11 – 14 gripping the coiled wire conductor 1 at the proximal end of the lead for rotating the helix 3 out of and back into the electrode head.

The electrode head at the distal end of the lead comprises a molded silicone rubber cover 7 connected or molded to the tubular silicone rubber sheath 2. The helix 3 comprises a section of the coiled wire conductor 1 with an extended pitch and sharpened tip. A platinum indicator ring 4 is enclosed by the cover 7 at the end of the sheath 2. A blocking plate covers the end of the sheath 2 within ring 4, except for a passage for the helix 3. The helix 3 extends within a cavity 15 and through the end of the cover 7. As in the preceding embodiments, the helix 3 may be extended from or retracted back into the cover 7 and sheath 2 by rotation of the conductor 1.

The cover 7 possesses a concave frontal surface through which the tip of the helix 3 just extends a distance of 0.008 inches, for example. This allows the lead to be advanced transvenously without damaging the blood vessels or heart valve.

It will be understood that the length of electrical conductor 1 and its insulating sheath 2 may be any length found appropriate in the prior art of cardiac pacing leads for the transvenous placement of the lead in the heart and attachment to a subcutaneously implanted pulse generator. In FIG. 4, only the distal electrode head and the proximal connector pin are shown in detail, the intermediate conductor portion being subtended for purposes of illustration.

The proximal end of the lead depicted in FIG. 4 comprises an insulating member 11 and a conductive connector pin 12 having a cavity 13 for receiving and enabling the electrical and mechanical connection to the distal end of the coil conductor 1. The member 11 and pin 12 are of known configurations and are dimensioned to snugly fit in the female connector of the pulse generator.

However, unlike prior art pacing leads, the insulating member 11 is not affixed to the proximal end portion of the sheath 2. Rather, in the retracted position depicted in FIG. 4, end surfaces of the sheath 1 and member 11 define an annular cavity 14. In the extended position of the helix 3, the end surfaces will contact, or nearly contact one another, filling the cavity 14.

In the surgical procedure, just prior to insertion of the lead, a medical adhesive is injected into the electrode head to fill the space 15 surrounding the helix 3. The medical adhesive will cure to form a water barrier over a period of time sufficient to complete the procedure. Thereafter, the lead is transvenously advanced by well known surgical techniques until the electrode head is butted against the endocardium in a desirable location. Threshold sensing and pacing measurements may be made through the tip of the helix extending through the concave surface. The electrode head may be repositioned until thresholds are satisfactory. Then, in accordance with the features of the invention, the helix may be advanced through the blocking plate 6 and the end surface of the cover 7 and screwed into the cardiac tissue by rotating the member 11 with respect to the sheath 2. The length of coil conductor 1 is thereby rotated and acts as a flexible transmission shaft to transmit rotational torque to the helix 3. The surgeon can feel increased resistance, indicating that the helix 3 is fully extended, when the coil 1 abuts the plate 6. Also he can note the advancement, on fluoroscopic display, of the helix 3 with respect to the ring 4.

By reversing the direction of rotation, the helix 3 can be unscrewed, and the lead can be repositioned. When the surgeon is satisfied, connection is made to the pulse generator and medical adhesive is applied to the exposed abutting surfaces of the member 11 and sheath 2.

In the preferred embodiments described above, the helix 3 may preferably have an outside diameter of about 0.05 inches and extend 0.2 inches in about six turns. The conductor itself may have a diameter of about 0.01 inches.

In order to keep as small as possible, in each embodiment of the invention, the area of conductive material contacting tissues, the invention further provides covering with an insulating layer, preferably of silicon rubber, those surfaces of the helix 3 of the electrode head which are not needed for the electrical stimulation.

Although a unipolar lead design has been illustrated in the description of the preferred embodiments, it will be understood that bipolar leads (that is leads carrying two electrodes and conductors) may as readily employ the novel electrode design of the present invention. It should be understood that although the use of the lead has been described for use in a cardiac pacing system, the lead could as well be applied to other types of body stimulating systems.

It should be further understood, of course, that the foregoing disclosure relates only to the best modes known to the inventor of many possible modes of practicing the invention and that numerous modifications may be made therein without departing from the spirt and scope of the invention as set forth in the appended claims.

What is claimed is:

1. A body-implantable lead of materials substantially inert to body fluids and tissue comprising:
   a length of electrical conductor having proximal and distal ends;
   an electrode connected to the distal end of said conductor, said electrode having tissue engaging means for securely engaging said electrode in contact with body tissue;
   sheath means having proximal and distal ends for loosely receiving and insulating said conductor from body tissue, said conductor being adapted to be axially advanced from its proximal end in and relative to said sheath means; and
   electrode head means attached to the distal end of said sheath means for receiving and isolating said electrode from body fluids and tissue, said electrode head means further comprising means for loosely engaging at least a portion of said electrode and for allowing the axial advancement of said electrode a predetermined distance from said sheath means upon advancement of said conductor in and relative to said sheath means.

2. The body-implantable lead of claim 1 wherein said electrode further comprises:
   a helix having a tissue piercing tip and a number of tissue engaging turns, said helix being electrically connected to the distal end of said conductor and adapted to be advanced from said electrode head means and screwed into body tissue, to firmly lodge in and permanently secure said electrode to the body tissue, upon rotation in one direction of the proximal end of said conductor.

3. The body-implantable lead of claim 2 wherein said engaging means contacts at least one turn of said helix for allowing advancement and retraction of said helix from said sheath means only by rotation of said conductor with respect to said sheath means.

4. The body-implantable lead of claim 2 wherein said electrode head means further comprises:
   a block of material filling a portion of the distal end of said sheath means having a helical passage for receiving said helix, the passage having a pitch and dimensions comparable to those of said helix.

5. The body-implantable lead of claim 2 wherein said engaging means further comprises:
   at least one nonconductive wire traversing said electrode head means and the space between adjacent turns of said helix.

6. The body-implantable lead of claim 2 wherein said electrode head means further comprises:
   a cylindrical head of dimensions sufficient to enclose said helix contacting at one end the distal end of said sheath means and having across its other end a sheath of material through which the tissue piercing tip and the tissue engaging turns of said helix may be advanced.

7. The body-implantable lead of claim 1 wherein said conductor further comprises:

a length of closely wound helical conductor; and said electrode further comprises:

a helix having a tissue piercing tip and a number of tissue engaging turns, said helix being electrically connected to the distal end of said conductor and adapted to be advanced from said electrode head means and screwed into body tissue, to firmly lodge in and permanently secure said electrode to the body tissue, upon rotation in one direction of the proximal end of said conductor.

8. The body-implantable lead of claim 7 wherein said helix further comprises the distal end portion of said length of helical conductor loosely wound for a predetermined number of turns.

9. The body-implantable lead of claim 8 wherein said helical coiled conductor has a first outside diameter and said helix has a second outside diameter greater than the first outside diameter.

10. The body-implantable lead of claim 1 further comprising:

a ring of a material opaque to X-rays placed at the distal end of said sheath means and coated with an insulating material so that the respective locations of the electrode and the sheath means may be ascertained by X-ray inspection.

11. The body-implantable lead of claim 1 wherein said electrode head means further comprises:

means for loosely engaging a portion of said electrode.

12. The body-implantable lead of claim 1 wherein said conductor further comprises:

a length of closely wound helical coil wire having a predetermined winding pitch and outside diameter; and said sheath means further comprises:

means for engaging the outside surface presented by the coils of said conductor for a portion of the conductor's length by enabling axial advancement and retraction of said conductor in said sheath means by rotation of said conductor with respect to said sheath means.

13. The body-implantable lead of claim 12 wherein said engaging means further comprises:

spiral groove means of a pitch approximately equal to that of said helical coil conductor for engaging the outside surface thereof.

14. The body-implantable lead of claim 1 wherein said sheath means further comprises:

a second length of electrical conductor having proximal and distal ends;

a layer of electrically insulating material overlying the outer surface presented by said second length of electrical conductor; and an uninsulated ring electrode of dimensions generally corresponding to those of said second electrical conductor attached at the distal end of said second electrical conductor.

15. The body-implantable lead of claim 14 wherein:

said first and second lengths of electrical conductor make electrical contact for commonly conducting electrical signals to and from said ring electrode.

16. The body-implantable lead of claim 14 wherein said electrode comprises:

a helix having a tissue piercing tip and a number of tissue engaging turns, said helix being electrically connected to the distal end of said first length of electrical conductor and adapted to be advanced from said electrode head means and screwed into body tissue, to firmly lodge in and permanently secure said electrode to the body tissue, upon rotation in one direction of the proximal end of said first length of electrical conductor.

17. The body-implantable lead of claim 16 wherein:

said helix is formed of the distal end portion of said first length of electrical conductor loosely wound and enlarged in outside diameter; and wherein:

said second length of electrical conductor is likewise enlarged in diameter at the distal end thereof an amount sufficient to form said electrode head means and enclose said helix.

18. The body-implantable lead of claim 14 wherein said second length of electrical conductor comprises a tightly wound coil having a predetermined pitch and inside and outside diameters; and wherein:

said first length of conductor has an outside diameter approximately equal to the inside diameter of said second length of conductor;

said first length of electrical conductor is coaxially extended within said second length of conductor, the respective wound coils loosely engaging each other.

19. The body-implantable lead of claim 1 further comprising:

connector means for connecting said lead to an electrical device, said connector means being electrically and mechanically connected to the proximal end of said conductor and spaced from said sheath means.

20. The body-implantable lead of claim 19 wherein said electrode further comprises:

a helix having a tissue piercing tip and a number of tissue engaging turns, said helix being electrically connected to the distal end of said conductor and adapted to be advanced from said electrode head means and screwed into body tissue, to firmly lodge in and permanently secure said electrode to the body tissue, upon rotation in one direction of said connector means with respect to said sheath means and said electrode head means.

21. The body-implantable lead of claim 1 wherein said electrode head means further comprises:

means for contacting said electrode as it is advanced from said electrode head means to inhibit the ingress of body fluids within said electrode head means.

* * * * *